US010463811B2

(12) United States Patent
Lee et al.

(10) Patent No.: US 10,463,811 B2
(45) Date of Patent: Nov. 5, 2019

(54) DISPENSER FOR SPRAYING POWDER AND POWDER SPRAYER INCLUDING SAME

(71) Applicant: NEXTBIOMEDICAL CO., LTD., Incheon (KR)

(72) Inventors: Don Haeng Lee, Seoul (KR); Jong Chae Park, Sejong (KR); Eunhye Lee, Incheon (KR); Keun Su Kim, Incheon (KR)

(73) Assignee: NEXTBIOMEDICAL CO., LTD., Incheon (KR)

( * ) Notice: Subject to any disclaimer, the term of this patent is extended or adjusted under 35 U.S.C. 154(b) by 27 days.

(21) Appl. No.: 15/510,044

(22) PCT Filed: Sep. 22, 2015

(86) PCT No.: PCT/KR2015/009946
§ 371 (c)(1),
(2) Date: Mar. 9, 2017

(87) PCT Pub. No.: WO2016/048006
PCT Pub. Date: Mar. 31, 2016

(65) Prior Publication Data
US 2017/0296760 A1 Oct. 19, 2017

(30) Foreign Application Priority Data
Sep. 22, 2014 (KR) ........................ 10-2014-0125908

(51) Int. Cl.
*A61M 11/02* (2006.01)
*A61M 11/00* (2006.01)
(Continued)

(52) U.S. Cl.
CPC ............. *A61M 11/02* (2013.01); *A61M 11/00* (2013.01); *A61M 13/00* (2013.01); *A61M 35/00* (2013.01);
(Continued)

(58) Field of Classification Search
CPC ... B05B 1/3026; B05B 7/0012; B05B 7/1404; B05B 7/1413; B05B 7/1422;
(Continued)

(56) References Cited

U.S. PATENT DOCUMENTS 1,988,017 A 1/1935 Norwick
2,570,774 A 10/1951 Davis
(Continued)

FOREIGN PATENT DOCUMENTS

JP 07-155377 A 6/1995
JP 11-104149 4/1999 ............. A61C 3/025
(Continued)

OTHER PUBLICATIONS

Notice of Allowance from corresponding Korean Application No. KR 10-2015-0134007 dated Feb. 27, 2017, and its English translation.

(Continued)

*Primary Examiner* — Cody J Lieuwen
(74) *Attorney, Agent, or Firm* — Harness, Dickey & Pierce, P.L.C.

(57) ABSTRACT

The present invention provides a 2-way air flow type dispenser for spraying powder and a powder sprayer including the same. The present invention adopts a 2-way air flow manner in which an air flow causing the powder to be sprayed and an air flow causing the powder to be transferred from a container to a spraying nozzle are separately formed, thereby enabling the smooth spraying of the powder.

7 Claims, 13 Drawing Sheets

(51) Int. Cl.
*A61M 13/00* (2006.01)
*A61M 35/00* (2006.01)
*B05B 7/14* (2006.01)
*B05B 7/16* (2006.01)

(52) U.S. Cl.
CPC .......... *B05B 7/1422* (2013.01); *B05B 7/1486* (2013.01); *A61M 2202/064* (2013.01); *A61M 2205/0216* (2013.01); *A61M 2205/36* (2013.01); *A61M 2205/8206* (2013.01); *A61M 2205/8237* (2013.01); *B05B 7/1613* (2013.01)

(58) Field of Classification Search
CPC ... B05B 7/1463; B05B 7/1481; B05B 7/1486; B05B 7/1613; B05B 7/14; A61M 11/02; A61M 2202/064; A61M 2205/0216; A61M 2205/36; A61M 2205/8206; A61M 2205/8237; A61M 11/00; A61M 13/00; A61M 35/00
USPC ........ 239/144, 373, 375–379, 414, 433–434, 239/654, 655, 413, 415; 604/58
See application file for complete search history.

(56) References Cited

U.S. PATENT DOCUMENTS

| 3,746,254 | A | * | 7/1973 | Duncan ................ B05B 5/032 239/697 |
| 4,184,258 | A | * | 1/1980 | Barrington ............ A61C 3/025 222/636 |
| 4,635,852 | A | | 1/1987 | Muhlnickel, Jr. |
| 5,445,612 | A | | 8/1995 | Terakura et al. .............. 604/58 |
| 5,951,531 | A | | 9/1999 | Ferdman et al. |
| 2009/0000615 | A1 | | 1/2009 | Pohlmann et al. ...... 128/200.21 |
| 2010/0065048 | A1 | | 3/2010 | Mueller-Walz et al. |
| 2011/0251580 | A1 | * | 10/2011 | Greenhalgh ........... A61M 11/00 604/500 |
| 2013/0218072 | A1 | * | 8/2013 | Kubo ..................... A61M 11/06 604/58 |
| 2015/0075527 | A1 | | 3/2015 | Iwatschenko et al. .. 128/203.15 |

FOREIGN PATENT DOCUMENTS

| JP | 2012-143502 | | 8/2012 | ........... A61M 13/00 |
| JP | 2012-161523 | A | 8/2012 | |
| KR | 10-0329333 | | 11/2002 | ........... A61M 35/00 |
| KR | 10-0791398 | | 1/2008 | ............... A61J 3/02 |
| KR | 2008-0003394 | A | 1/2008 | |
| KR | 10-2012-0023668 | | 3/2012 | ........... A61M 15/00 |
| KR | 10-2012-0135012 | | 12/2012 | ........... A61M 11/00 |
| KR | 20120135012 | A | * 12/2012 | |
| KR | 10-1379999 | | 4/2014 | ........... A61M 11/00 |
| RU | 2468739 | C1 | 12/2012 | |

OTHER PUBLICATIONS

Extended European Search Report from corresponding European Patent Application No. 15843103.1, dated May 7, 2018.
Australian Office Action from corresponding Australian Patent Application No. 2015322357, dated Feb. 26, 2018.
Japanese Office Action from corresponding Japanese Patent Application No. 2017-515045 dated Feb. 6, 2018, and it's English translation.
International Search Report (ISR) in PCT/KR2015/009946, dated Jan. 11, 2016 published in WO 2016/048006.
Notice of Allowance from corresponding Japanese Patent Application No. 2017-515045, dated Jul. 3, 2018, and it's English translation.
Office Action from corresponding Russian Patent Application No. 2017107742, dated Jun. 6, 2018, and it's English translation.

* cited by examiner

DISPENSER FOR SPRAYING POWDER AND POWDER SPRAYER INCLUDING SAME

CROSS-REFERENCE TO RELATED APPLICATIONS

This application is a national phase application of PCT Application No. PCT/KR2015/009946, filed on Sep. 22, 2015, which claims the benefit and priority to Korean Patent Application No. 10-2014-0125908, filed Sep. 22, 2014. The entire disclosures of the applications identified in this paragraph are incorporated herein by references.

FIELD

The present invention relates to a 2-way air flow type dispenser for powder spray and a powder sprayer including the same.

BACKGROUND

Bleeding management is important during surgery. Blood loss may cause innumerable problems in patients, whereas the presence of blood at undesirable locations is harmful to normal tissues or may impede the ability of doctors who check the surgery sites. This bleeding may also be problematic even during the minimally invasive surgical procedure (e.g., laparoscopic surgery).

Gastrointestinal bleeding is a frequently encountered clinical problem. At least 80% of gastrointestinal bleeding cases occur in the upper gastrointestinal tract. The upper gastrointestinal tract bleeding refers to a disease in which lesions of esophagus, stomach, and duodenum are bleeding, causing blood vomiting or bloody excrement. The endoscopy can confirm bleeding lesions in 90% or more of gastrointestinal tract bleeding cases, and 40-50% of gastrointestinal tract bleeding cases are known to be caused by stomach ulcers or duodenum bleeding.

In recent years, gastric or colorectal polypectomy or mucosectomy and endoscopic operation for the treatment of early gastric cancer and colorectal cancer have been frequently conducted. During or after these operations, the bleeding causes people to receive emergency surgery or even to die.

In recent years, endoscopic hemostasis has been increasingly used to treat bleeding and gastrointestinal bleeding during the surgical procedure, bleeding occurring when tissue is taken for histological examination, and the like. The hemostasis using an endoscope is conducted by approaching an in vivo inserted endoscopic conduit (catheter) to a mucosal lesion in need of hemostasis and then administering and spraying an appropriate hemostatic agent through the conduit.

Medical powder sprayers have been developed to achieve this purpose. One of the medical powder sprayers, using the same principle as a coating spray, is operated in such a manner that a hemostatic agent is injected into a tube provided in a sprayer and then compressed air is supplied to the tube to spray and apply the hemostatic agent to the lesion. However, in such a powder sprayer, having too little of the drug that is charged in the tube cannot give an effective therapeutic effect, while having too much of the drug causes the clogging of the tube and thus the drug is not sprayed.

A powder spray device that improves such a powder sprayer is disclosed in Korean Patent Registration No. 10-0329333. The powder spray device is operated in such a manner that a drug container is mounted upside down on the top of an apparatus and then air is supplied into the drug container, so that the air introduced into the drug container disturbs the drug in the drug container and discharged to a discharge port together with the drug.

The powder spray device reduces the clogging of the conduit and enhances the spraying power as compared with a conventional sprayer adopting a coating spray manner, but the powder spray device is operated in a 1-way air flow manner in which the air moving into the drug container causes the discharge of a powdered drug out of the drug container and the spray of the powdered drug through the conduit, and thus it has difficulty in obtaining satisfactory spraying power.

In the case of using the powder sprayer, water may flow back to the medical conduit inserted into the body since water, such as body fluid, exists in the body, and a powder having high hygroscopicity clumps together due to the moisture, causing a risk of clogging the conduit. The moisture that comes into the conduit is difficult to remove due to the surface tension, but the conventional powder sprayers including the powder spray device have no technical means to solve the problems.

Throughout the entire specification, many papers and patent documents are referenced and their citations are represented. The disclosure of the cited papers and patent documents are entirely incorporated by reference into the present specification, and the level of the technical field within which the present invention falls and the details of the present invention are described more clearly.

DETAILED DESCRIPTION

Technical Problem

Under these circumstances, the present inventors developed: a 2-way air flow type dispenser for powder spray, which solves the clogging of a conduit due to the clumping of a powder and the back flow of the water into the conduit, which occurs when a powdered drug is sprayed and applied into the body through a medical conduit; and a powder sprayer including the same.

Accordingly, an aspect of the present invention is to provide a dispenser for powder spray.

Another aspect of the present invention is to provide a powder sprayer including the dispenser for powder spray.

Other purposes and advantages of the present invention will become more obvious with the following detailed description of the invention, claims, and drawings.

Technical Solution

In accordance with an aspect of the present invention, there is provided a dispenser for powder spray detachably installed on a sprayer main body, which generates a flow of air for powder spray, to spray a powder to a target site using the flow of air supplied from the sprayer main body, the dispenser for powder spray including: a dispenser coupling unit provided to detachably couple the dispenser to the sprayer main body; a conduit mount unit provided in one end to accommodate a conduit for guiding the powder to a target site; a container accommodation unit provided in an upper end of the dispenser to accommodate the container containing the powder; a powder discharge port provided in a lower end of the container accommodation unit to transfer the powder in the container accommodation unit to a lower space; an air inlet formed to be spaced from the powder discharge port by a predetermined distance to transfer air to the container accommodation unit; and an air movement and mixing tube provided adjacent to the conduit mount unit, the air movement and mixing tube including: a guide tube for guiding the flow of air supplied from the sprayer main body toward the conduit mount unit; a first passage extended from the guide tube toward the air inlet to guide the air inside the guide tube toward the container accommodation unit; and a second passage extended from the guide tube toward the powder discharge port to accommodate the powder, which has passed through the powder discharge port, in the guide tube.

According to an embodiment of the present invention, the powder may be a drug.

According to an embodiment of the present invention, the dispenser for powder spray may be a medical dispenser for powder spray equipped with a medical conduit inserted into the body.

According to an embodiment of the present invention, the dispenser for powder spray may further include an opening and closing control unit provided between the air movement and mixing tube and the container accommodation unit to move back and forth to shift the locations of two holes that are provided, thereby simultaneously controlling the communication between the first passage and the air inlet and the communication between the second passage and the powder discharge port.

In a particular embodiment, the opening and closing control unit may include: a slider having the two holes and moving back and forth; a slider guide groove for guiding the movement of the slider; and an elastomer for returning the moved slider to the original location.

According to another embodiment of the present invention, the dispenser for powder spray may further include an air distributor inserted inside the air movement and mixing tube and having two holes for guiding the flow of air supplied from the sprayer main body toward the first passage and the conduit mount unit, separately.

According to an embodiment of the present invention, the sprayer main body may include: a power unit for supplying power to the sprayer main body; a main body coupling unit coupled with the dispenser coupling unit; a switch unit inducing the spray of the powder; an air generation unit for generating the flow of air in the apparatus according to the operation of the switch unit; and an air supply tube extended from the air generation unit to guide the generated flow of air to the air movement and mixing tube.

In a particular embodiment, the sprayer main body may further include a horizontal transfer movement unit for horizontally transferring the opening and closing control unit.

According to an embodiment of the present invention, the switch unit may include: a main switch for operating the air generation unit to move the air toward the conduit mount unit; and an operation switch for operating the horizontal transfer movement unit so as to spray the powder by the flow of air generated according to the operation of the main switch, thereby simultaneously performing the communication between the first passage and the air inlet and the communication between the second passage and the powder discharge port.

According to an embodiment of the present invention, in the dispenser for powder spray, vibrators for vibrating the powder in the container accommodation unit may be installed adjacent to the container accommodation unit.

According to an embodiment of the present invention, vibrators for vibrating the powder in the container accommodation unit may be provided in the main body.

According to an embodiment of the present invention, the air generation unit may further include a heating apparatus for air heating.

According to an embodiment of the present invention, the sprayer main body may include a vibrator operation unit for operating the vibrators.

In accordance with an aspect of the present invention, there is provided a powder sprayer including the above-described dispenser for powder spray.

The powder sprayer may include a sprayer main body, which has been described above.

Advantageous Effects

Features and advantages of the present invention are summarized as follows:

(1) The present invention provides a 2-way air flow type dispenser for powder spray and a powder sprayer including the same.

(2) The present invention adopts a 2-way air flow manner in which the air flow inducing the spray of the powder and the air flow inducing the transfer of the powder to the spray nozzle from the container are separately carried out, thereby achieving a smooth spray of the powder.

(3) The present invention can adopt a 2-way air flow manner in which, even while the powder is not sprayed, the air is continuously moved in a direction of the conduit to prevent the inflow of the moisture into the conduit, and when the powder needs to be sprayed, a part of the air is directed toward the container containing the powder to move the powder toward the conduit, thereby inducing the spray of the powder by the flow of the air continuing to move.

(4) The present invention can spray the powder to a target site without clogging by further including vibrators to increase the flowability of the powder.

(5) The present invention can prevent the clumping of the powder due to the moisture by further including a heating apparatus to spray the powder using the moisture-free air.

(6) The present invention can be favorably utilized in inserting a drug, such as a hemostatic agent, into the body.

BRIEF DESCRIPTION OF THE DRAWINGS

FIG. 1 is an exploded perspective view showing a main structure of a dispenser for powder spray according to an embodiment of the present invention.

FIG. 2 is a cross-sectional view of the dispenser of FIG. 1 cut in a vertical direction.

FIG. 3 is a view of an upper part of the dispenser as seen from below.

FIG. 4 is a view of a lower part of the dispenser as seen from above.

FIG. 5 provides a front view (a) and an exploded perspective view (b) for showing a main structure of a dispenser coupling unit according to an embodiment of the present invention.

FIG. 6 is a perspective view for showing a dispenser coupling unit according to another embodiment of the present invention.

FIG. 7 is a view showing a main structure of an opening and closing control unit provided in a dispenser for powder spray according to another embodiment of the present invention.

MODE FOR CARRYING OUT THE INVENTION

Hereinafter, preferred embodiments of the present invention will be described in detail with reference to the accompanying drawings. However, the present invention is not restricted or limited to the embodiments. For reference, like numerals substantially refer to like elements throughout the present specification, and can be described by referring to the contents described in other drawings in the following description, and the contents that are determined to be apparent to those skilled in the art or that are repeated may be omitted.

The preferred embodiments of the present invention are capable of having various modifications and alternative forms, and particular embodiments of the present invention will be illustrated in the attached drawings and described in this specification in detail. It should be understood, however, that there is no intent to limit embodiments of the invention to the particular forms disclosed, but on the contrary, embodiments of the invention are to cover all modifications, equivalents, and alternatives falling within the technical idea and scope of the present invention.

Hereinafter, a dispenser for powder spray and a powder sprayer including the same according to an embodiment of the present invention will be described in detail with reference to the drawings.

Figure 1:
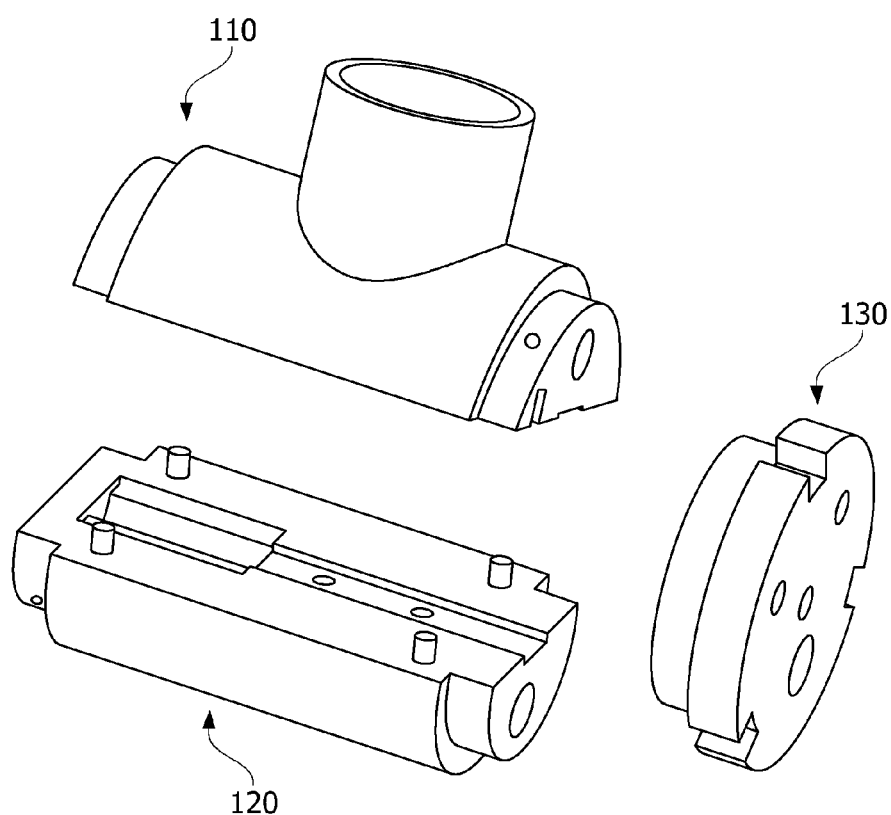
Figure 2:
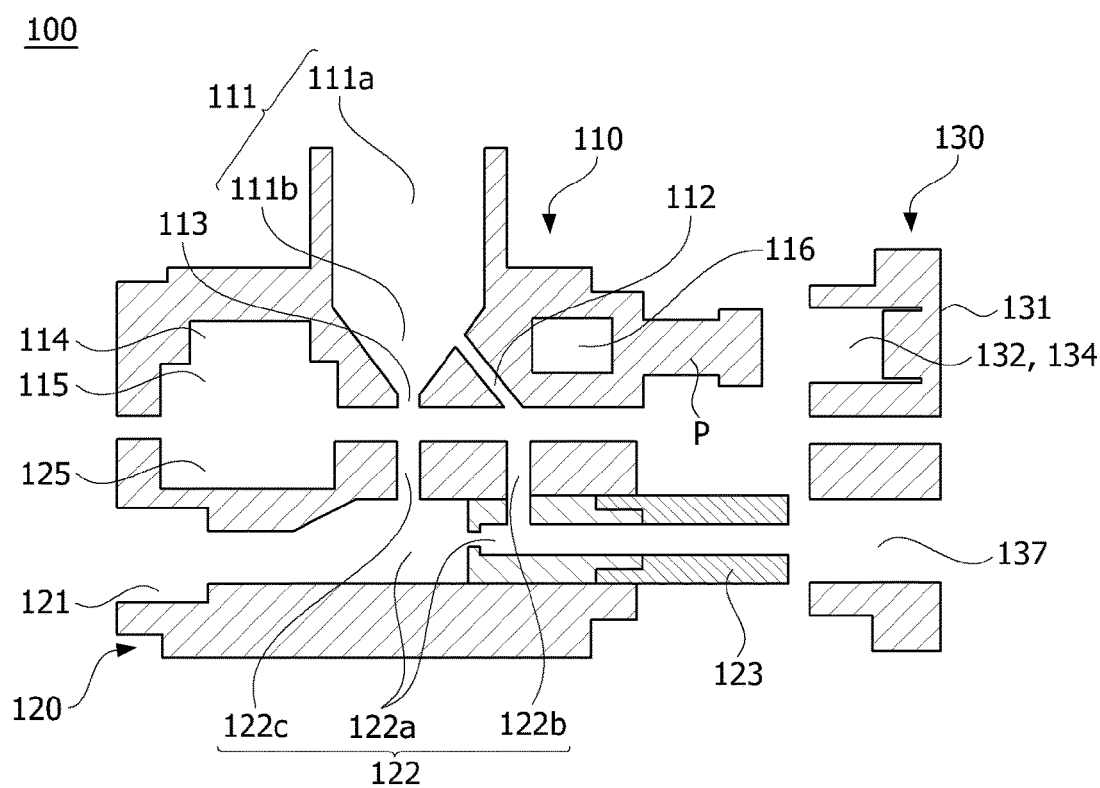
Figure 3:
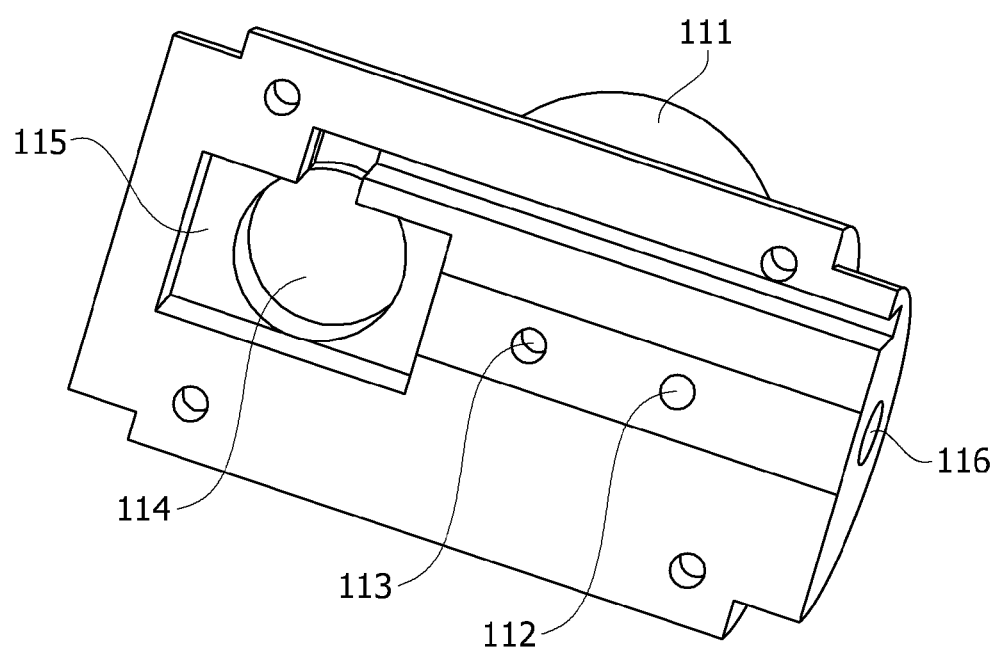
Figure 4:
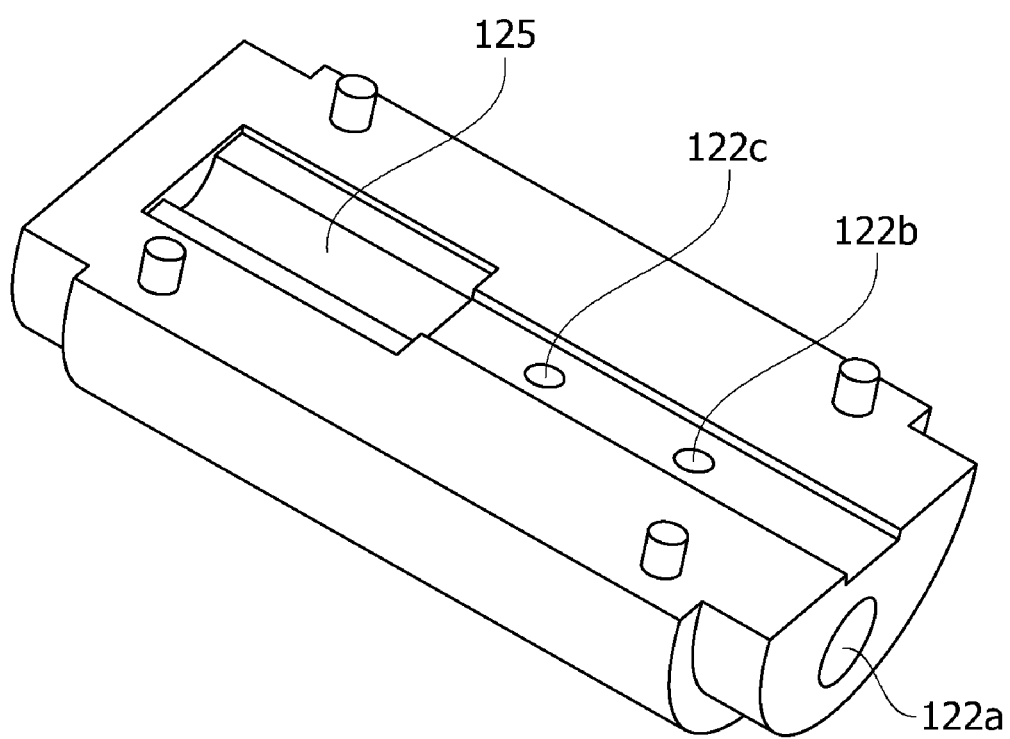
Figure 5:
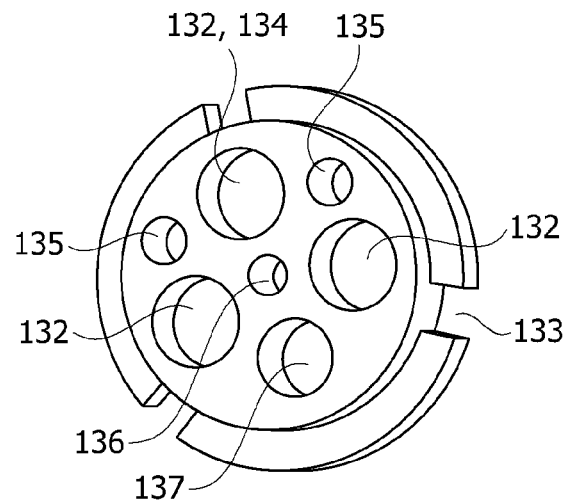
Figure 5:
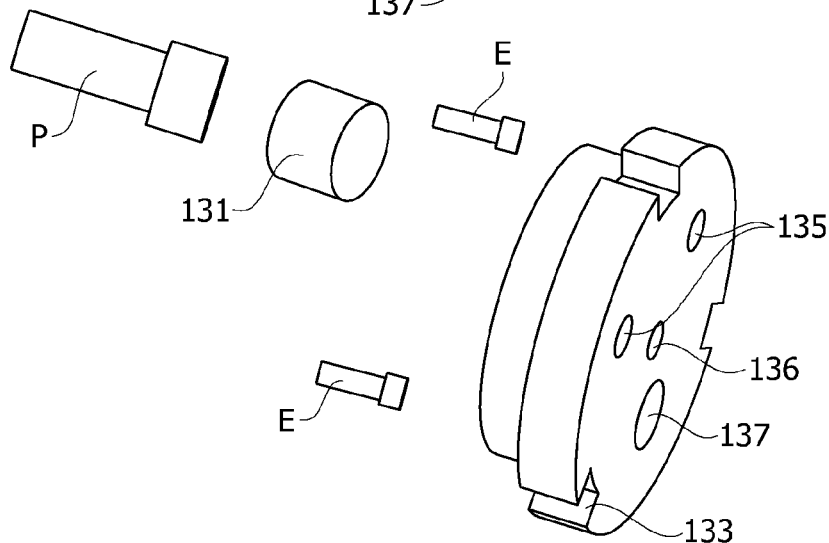

FIG. 1 is an exploded perspective view showing a main structure of a dispenser for powder spray according to an embodiment of the present invention; FIG. 2 is a sectional view of the dispenser of FIG. 1 cut in a vertical direction; FIG. 3 is a bottom view of an upper part of the dispenser as seen from below; FIG. 4 is a view of a lower part of the dispenser as seen from above; and FIG. 5 is a perspective view showing a main structure of a dispenser coupling unit.

Referring to FIG. 1, a dispenser 100 for powder spray according to an embodiment of the present invention is mainly divided into a dispenser upper part 110, a dispenser lower part 120, and a dispenser coupling unit 130.

The dispenser upper part 110 will be described with reference to FIGS. 2 and 3.

As shown in the drawings, the dispenser upper part 110 includes a container accommodation unit 111, an air inlet 112, and a powder discharge port 113.

The container accommodation unit 111 is provided in the upper end of the dispenser 100. The container accommodation unit 111 includes: a container mount region 111a in which a container containing a powder is mounted; and a chamber 111b provided below the container mount region 111a to collect and mix the powder flowing out from the container. When the container is mounted in the container mount region 111a, the powder in the container flows down to the chamber 111b by gravity.

For example, the container mount region 111a may be implemented in a thread shape so that a container (e.g., a vial) containing a powder to be sprayed can be mounted in a screwing type, and the chamber 111b may be implemented in a cone shape for the smooth movement of the powder.

The air inlet 112 is an air movement passage provided toward the container accommodation unit 111 at the position spaced apart from the powder discharge port 113 by a predetermined distance so as to transfer the air, which has passed through the first passage 122b, to the container accommodation unit 111.

In an embodiment, the air inlet 112 directly communicates with the first passage 122b.

In another embodiment, the air inlet 112 communicates with the first passage 122b according to the operation of an opening and closing control unit 140 to be described later.

In still another embodiment, the air flows into the air inlet 112 through a hole provided in the air distributor 124 to be described later and the first passage 122b, without an opening and closing control unit 140.

The powder discharge port 113 is a powder and air movement passage provided in the lower end of the chamber 111b to transfer the powder, which has flown down to the chamber 111b of the container accommodation unit 111, toward a second passage 122c.

In an embodiment, the powder discharge port 113 directly communicates with the second passage 122c.

In another embodiment, the powder discharge port 113 communicates with the second passage 122c according to the operation of the opening and closing control unit 140 to be described later.

In still another embodiment, the powder, which has passed through the powder discharge port 113 by the inflow of the air distributed through a hole provided in the air distributor 124 to be described later, is transferred to a guide tube 122a without the opening and closing control unit 140.

Furthermore, the dispenser upper part 110 may further include vibrators for smoothly performing the spray of the powder. The vibrators may be mounted to prevent a phenomenon in which the powder in the container accommodation unit 111 clumps together or the powder sticks to a wall surface of the container accommodation unit 111, thereby clogging the powder discharge port 113, failing to discharge the powder. In addition, the vibrators may prevent the clumping of the powder in a mixing chamber to be described later. Various small eccentric motor vibrators, such as a coin type and a bar type vibrator, or magnetic vibrators may be used.

To this end, in the dispenser upper part 110, a vibrator frame 114, in which the vibrators can be accommodated, may be provided at the position adjacent to the container accommodation unit 111, and a fixing plate frame 115, which is a space in which a fixing plate member 117 for preventing the falling down of the mounted vibrators is installed, may be provided below the vibrator frame 114.

The fixing plate member 117 may have a semi-circular groove, in which an elastomer of the opening and closing control unit 140 to be described later is accommodated.

Meanwhile, the dispenser upper part 110 may have a holding pin hole 116 into which a holding pin P for fixing the dispenser coupling unit 130 to a coupled body of the dispenser upper part 110 and the dispenser lower part 120 is inserted.

Hereinafter, the dispenser lower part 120 of the dispenser 100 will be described with reference to FIGS. 2 and 4.

As shown in the drawings, the dispenser lower part 120 may include a conduit mount unit 121 and an air movement and mixing tube 122.

The conduit mount unit 121 is provided at the end of the dispenser 100 to accommodate a conduit for guiding a powder to a target site.

The air movement and mixing tube 122 is a tube formed adjacent to the conduit mount unit 121. The air movement and mixing tube 122 includes: a guide tube 122*a* for guiding the flow of the air provided from the sprayer main body 200 toward the conduit mount unit 121; a first passage 122*b* extended from the guide tube 122*a* toward the air inlet 112 to transfer the air inside the guide tube 122*a* toward the container accommodation unit 111; and a second passage 122*c* extended from the guide tube 122*a* toward the powder discharge port 113 at the position spaced apart from the first passage 122*b* by a predetermined distance to accommodate the powder, which has passed through the powder discharge port 113, in the guide tube 122*a*.

Due to the above structural characteristics, the air, which has been supplied from the sprayer main body 200 to the air movement and mixing tube 122, moves to the conduit, which is mounted in the conduit mount unit 121, via the guide tube 122*a* to generate the flow of the air in a direction of the conduit, and a part of the air moves toward the container accommodation unit 111 and 112 via the first passage 122*b*. The powder in the container accommodation unit 111 moves to the guide tube 122*a* (a mixing chamber to be described later) through the powder discharge port 113 by the air thus moved. As described above, the dispenser 100 of the present invention adopts a 2-way air flow manner.

The space inside the guide tube 122*a* positioned below the second passage 122*c* is a mixing chamber in which the air and the powder are mixed, the air being supplied from the sprayer main body 200, the powder being accommodated inside the guide tube 122*a* after passing through the powder discharge port 113 and the second passage 122*c*. The powder in a fluidization state inside the mixing chamber is pushed by the flow of the air inside the dispenser 100 and is sprayed to a target site (e.g., an in vivo bleeding site) through the conduit mounted in the conduit mount unit 121.

As shown in FIG. 2, the end of the guide tube 122*a* may be connected to the sprayer main body 200 via a connection tube 123 having elasticity, such as a silicon tube. Here, the connection tube 123 functions to buffer the transfer of the vibration, which is generated by the vibrators installed in the dispenser upper part 110, to the sprayer main body 200.

A spacer 125 in which an elastomer of the opening and closing control unit 140 to be described later is mounted may be provided in the upper end of the dispenser lower part 200.

Hereinafter, the dispenser coupling unit 130 will be described with reference to FIGS. 2 and 5.

The dispenser coupling unit 130 is an attaching and detaching unit for detachably coupling the dispenser 100 with the sprayer main body 200. This attaching and detaching unit can be implemented by a known coupling unit without limitation.

In an embodiment, the dispenser coupling unit 130, as shown in FIG. 5, is implemented by including: magnets 131 for being detachably coupled with the sprayer main body 200 using magnetic force; magnet fixing grooves 132 in which the magnets 131 are fixed; and coupling grooves 133 for fixing the movement in a radial direction upon the coupling with the sprayer main body 200.

The dispenser coupling unit 130 further includes: a holding pin fixing groove 134 for accommodating a holding pin P inserted into the holding pin hole 116 provided in the dispenser upper part 110; electrode pin holes 135 for accommodating electrode pins E for supplying power to the vibrators; a transfer shaft through hole 136 through which a transfer shaft 260*a* of a horizontal transfer movement unit 260 provided in the sprayer main body 200 passes; and a connection tube through hole 137 through which the connection tube 123 connecting between the guide tube 122*a* and the air supply tube 250 provided in the sprayer main body 200 passes.

In another embodiment, the dispenser coupling unit 130 may be implemented in the form of being coupled with one surface of the coupled body formed by coupling the dispenser upper part 110 and the dispenser lower part 120 as shown in FIGS. 2 and 5, and alternatively, the dispenser coupling unit 130 may also be detachably inserted into the groove 220 provided in the sprayer main body 200 as shown in FIG. 6.

FIG. 7 is a view showing a main structure of an opening and closing control unit provided in a dispenser for powder spray according to another embodiment of the present invention; and FIG. 8 is a view for illustrating the movement of air and a powder according to the operation of an opening and closing control unit.

Hereinafter, the opening and closing control unit 140 will be described with reference to FIGS. 7 and 8.

As shown in FIG. 7, the opening and closing control unit 140 is a linear member having a predetermined length. The opening and closing control unit 140 includes: a slider 141 having a hollow type slider air inlet 141*a* communicating with the air inlet 112 of the dispenser upper part 110 and a hollow type slider powder discharge port 141*b* spaced apart from the slider air inlet 141*a* by a predetermined distance and communicating with the powder discharge port 113 provided in the dispenser upper part 110; a slider guide groove 142 for guiding the backward or forward movement of the slider; and an elastomer 143 for returning the moved slider 141 to the original position thereof.

The end of the slider 141 is accommodated in the elastomer 143, such as a compression spring, and the elastomer 143 is installed in a fixing plate frame 115 provided at the dispenser upper part 110 while being inserted into the fixing plate 117 having a semi-circular groove. In addition, a portion of the elastomer 143 is located in a space 125 provided in the dispenser lower part 120.

The slider 141 is inserted into a slider guide groove 142 positioned between the dispenser upper part 110 and the dispenser lower part 120 to move backward and forward by the elastomer 143 and the horizontal transfer movement unit 260 provided in the sprayer main body 200.

One of the characteristics of the dispenser 100 according to the present invention, unlike a conventional powder sprayer, adopts a 2-way air flow manner in which, even while the powder is not sprayed, the air is continuously moved in a direction of the conduit to prevent the inflow of the water (e.g., fluid of the affected site) into the conduit, and when the powder needs to be sprayed, a part of the air is directed toward the container accommodation unit 111 to move the powder toward the conduit, thereby inducing the spray of the powder by the flow of the air continuing to move.

The 2-way air flow is controlled by the opening and closing control unit 140, and hereinafter, the movement of the powder and air according to the operation of the opening and closing control unit 140 will be described with reference to FIG. 8.

Figure 8A:
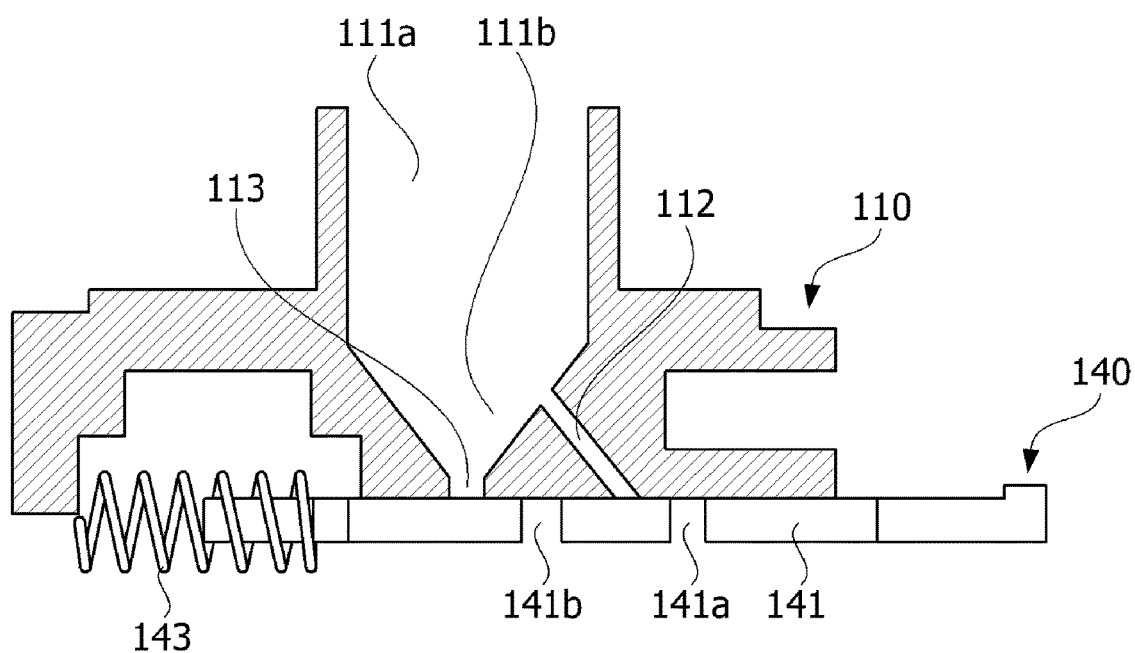
FIGS. 8a and 8b are cross-sectional views for illustrating the movement of air and a powder according to the operation of an opening and closing control unit.

FIG. 8*a* shows that the slider air inlet 141*a* formed in the slider 141 and the air inlet 112 provided in the dispenser upper part 110 do not match each other, and the slider powder discharge port 141*b* and the powder discharge port 113 provided in the dispenser upper part 110 do not match each other. In this condition, the movement of the air into the container accommodation unit 111 through the air inlet 112 and the movement of the powder into the mixing chamber in the guide tube 122*a* from the container accommodation unit are prevented.

Figure 8B:
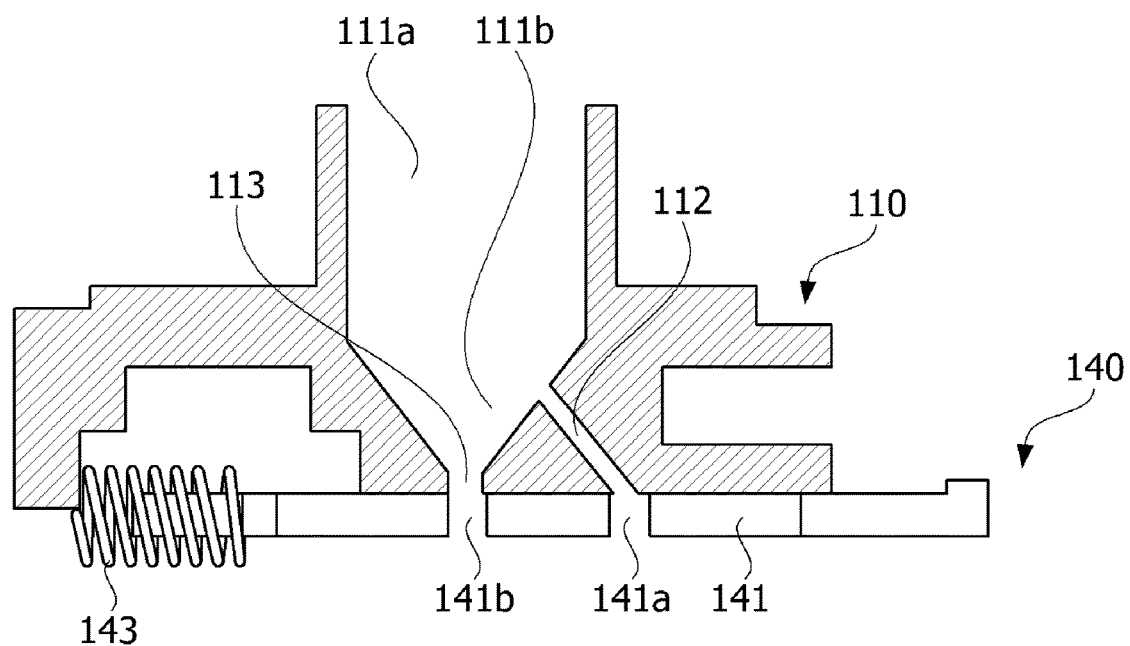

FIG. 8*b* shows that the slider 141 is moved by the horizontal transfer movement unit 260 according to the operation of the sprayer main body 200 such that the elastomer is pressed out, so the slider air inlet 141*a* and the air inlet 112 communicate with each other and the slider powder discharge port 141*b* and the powder discharge port 113 communicate with each other. In this condition, the air supplied from the sprayer main body 200 passes through the air inlet 112 and moves to the chamber 111*b* in the container accommodation unit 111, and the powder in the chamber 111*b* is transferred to the mixing chamber in the guide tube 122*a* via the powder discharge port 113, the slider powder discharge port 141*b*, and the second passage 122*c* by the air. The powder thus transferred into the mixing chamber is swept away in the air flowing from the guide tube 122*a* toward the conduit and is sprayed through the conduit.

Figure 9:
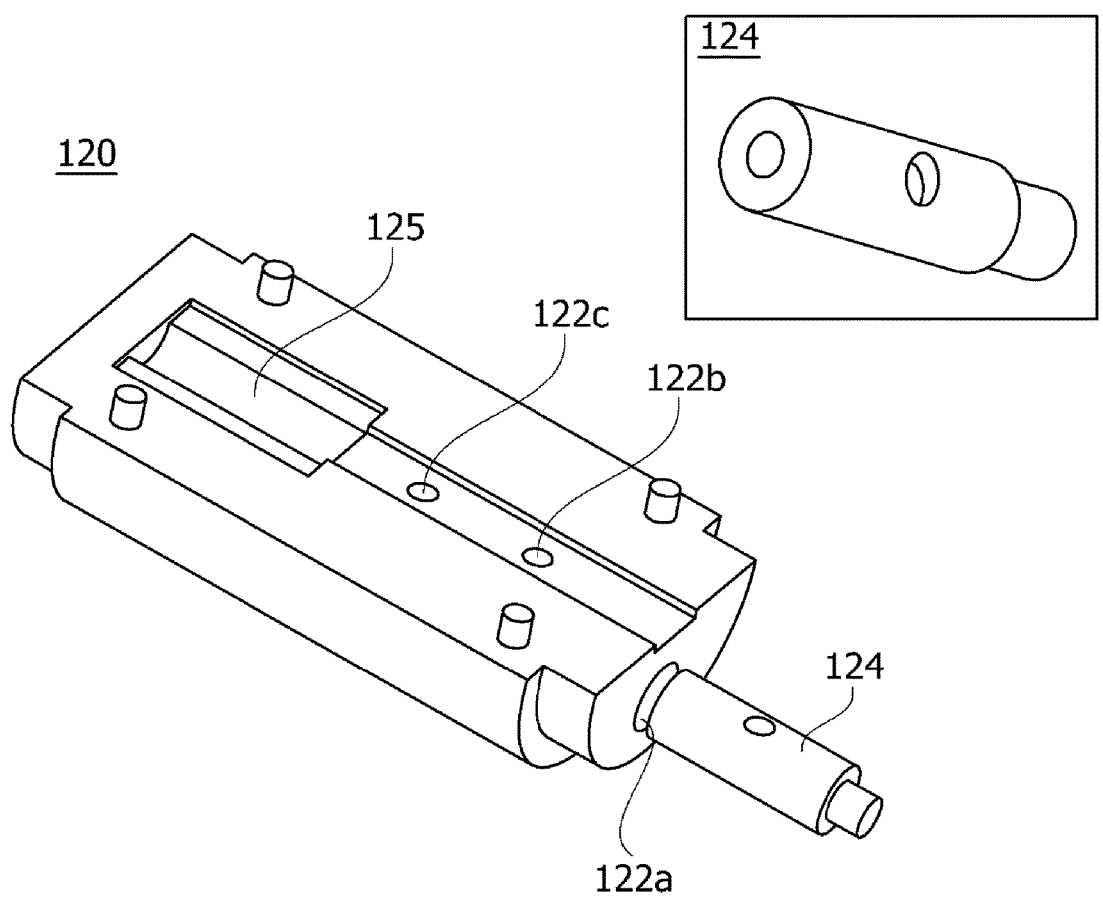
FIG. 9 is a view showing an air distributor provided in a dispenser for powder spray according to still another embodiment of the present invention.

FIG. 9 is a view showing an air distributor provided in a dispenser for powder spray according to still another embodiment of the present invention.

The air distributor 124 is a tube that has at least two holes for guiding the flow of air supplied from the sprayer main body 200 toward the first passage 122*b* and the conduit mount unit 121 while being inserted into the air movement and mixing tube 122 provided in the dispenser lower part 120. The amount of air moving into the mixing chamber, the amount of air leaking out to the first passage 122*b*, and/or the ratio between these amounts of air can be adjusted by the air distributor 124.

For example, the air distributor 124 has two holes toward the mixing chamber and the first passage 122*b*, and through the use of the air distributor 124, of which the holes have different sizes, the amounts of the air supplied to the mixing chamber and the first passage 122*b* can be adjusted to desired levels.

The air distributor 124 may be implemented in the same shape as the guide tube 122*a* such that the air distributor 124 can be easily inserted into the guide tube 122*a*, and the air distributor 124 may be inserted into the guide tube 122*a* to be located below the first passage 122*b* in the rear space of the mixing chamber.

If necessary, the air distributor 124 may be further extended toward the conduit mount unit 121, and an additional hole communicating with the second passage 122*c* may be provided in an upper end of the extended portion.

Figure 10:
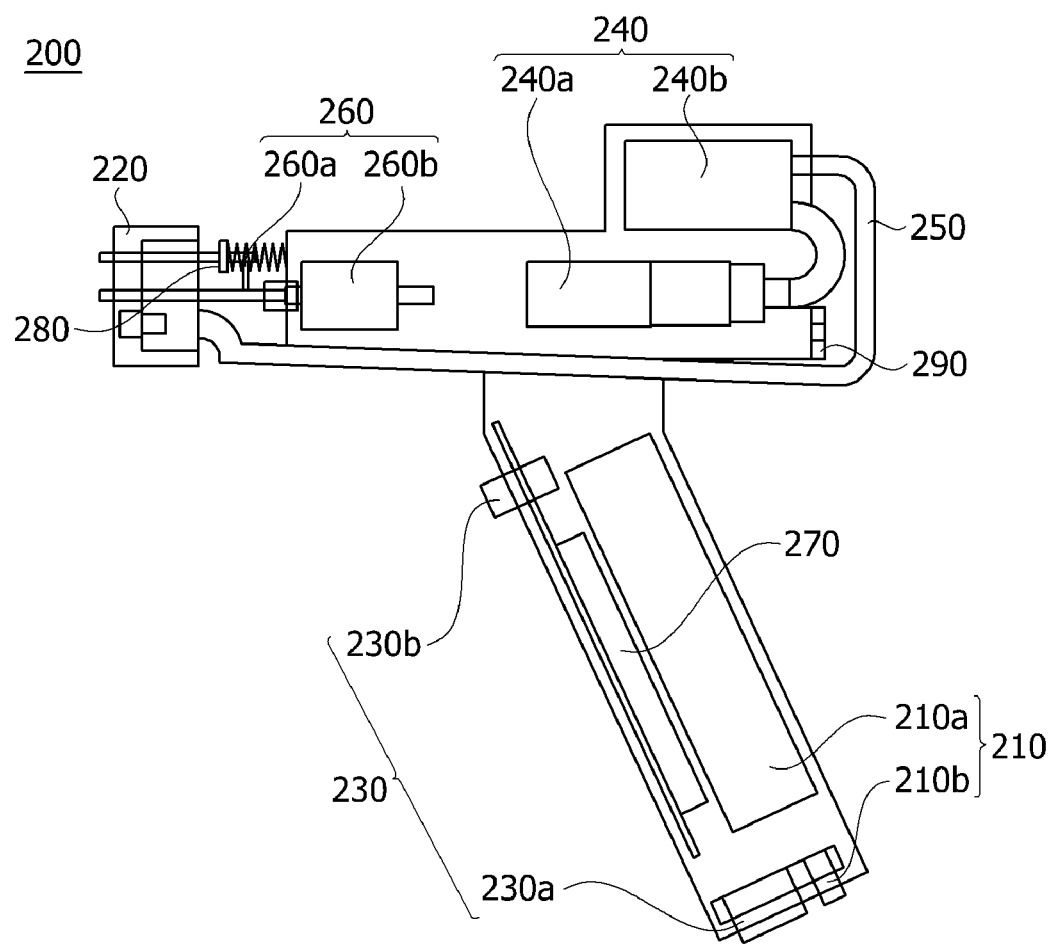
FIG. 10 is a schematic view showing a main structure of a sprayer main body coupled with a dispenser according to the present invention.
Figure 11:
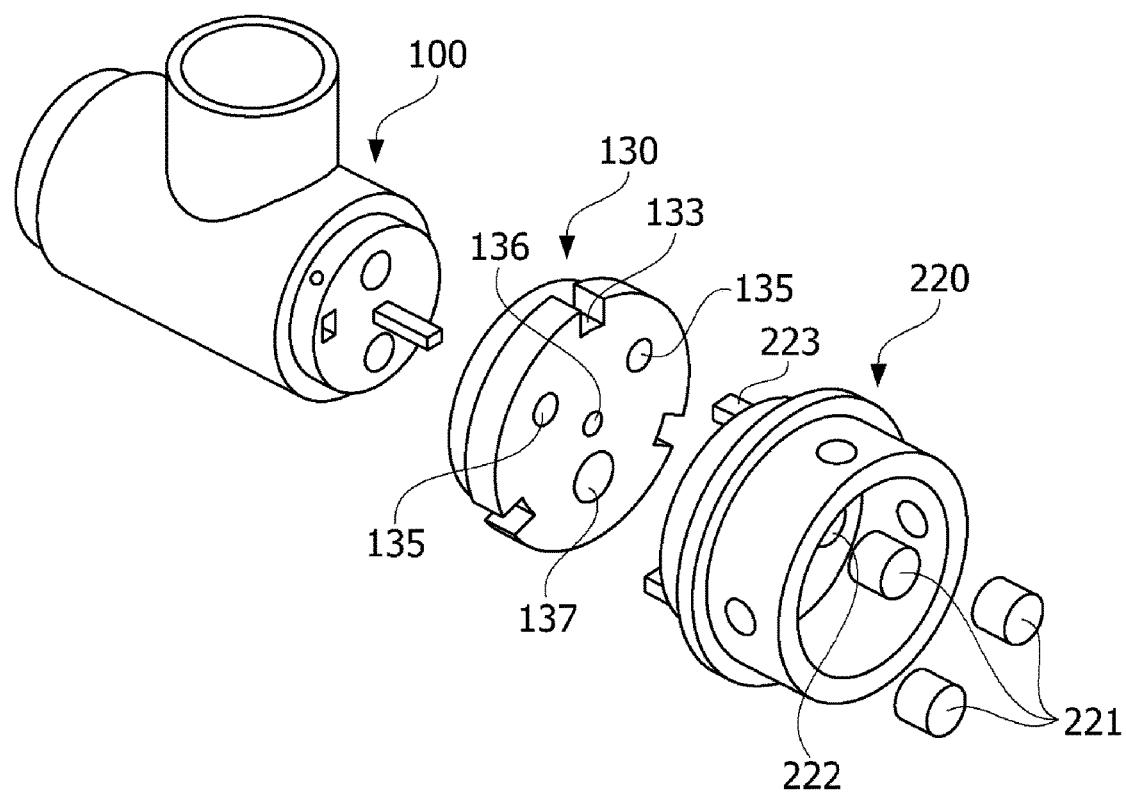
FIG. 11 is an exploded perspective view for illustrating the coupling between a sprayer main body and a dispenser.
Figure 12:
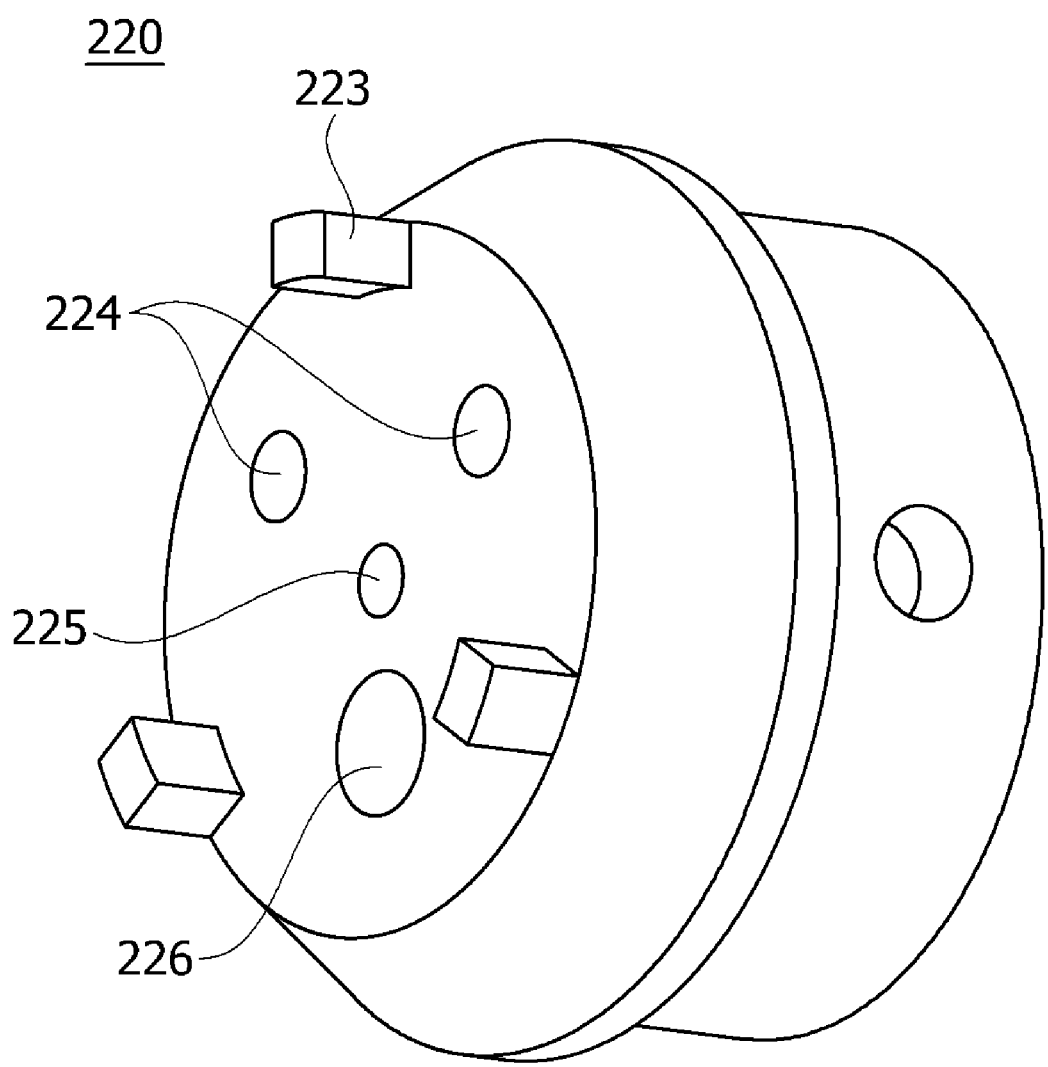
FIG. 12 is a perspective view showing a main structure of a sprayer main body coupling unit.

FIG. 10 is a schematic view showing a main structure of a sprayer main body according to an embodiment of the present invention coupled with the above-described dispenser; FIG. 11 is an exploded perspective view for explaining the coupling between the sprayer main body and the dispenser; and FIG. 12 is a perspective view showing a main structure of the sprayer main body coupling unit.

Referring to FIGS. 1 and 10, the sprayer main body 200 includes: a power unit 210 for supplying power to the sprayer main body 200; a sprayer main body coupling unit 220 coupled with the dispenser coupling unit 130; a switch unit 230 inducing the spray of the powder; an air generation unit 240 for generating the air flow in the apparatus according to the operation of the switch unit 230; and an air supply tube 250 extended from the air generation unit 240 to guide the flow of the generated air to the air movement and mixing tube 122 of the dispenser 100. The sprayer main body 200 may further include a horizontal transfer movement unit 260 for horizontally transferring the opening and closing control unit 140 provided in the dispenser 100.

The power unit 210 is for supplying power to the sprayer main body 200, furthermore the vibrators provided in the dispenser 100 or the sprayer main body 200, and may be implemented to supply direct current and/or alternating current (external power), and for example, may be implemented by a rechargeable battery 210*a* and a terminal 210*b* for battery charging and external power.

Figure 6:
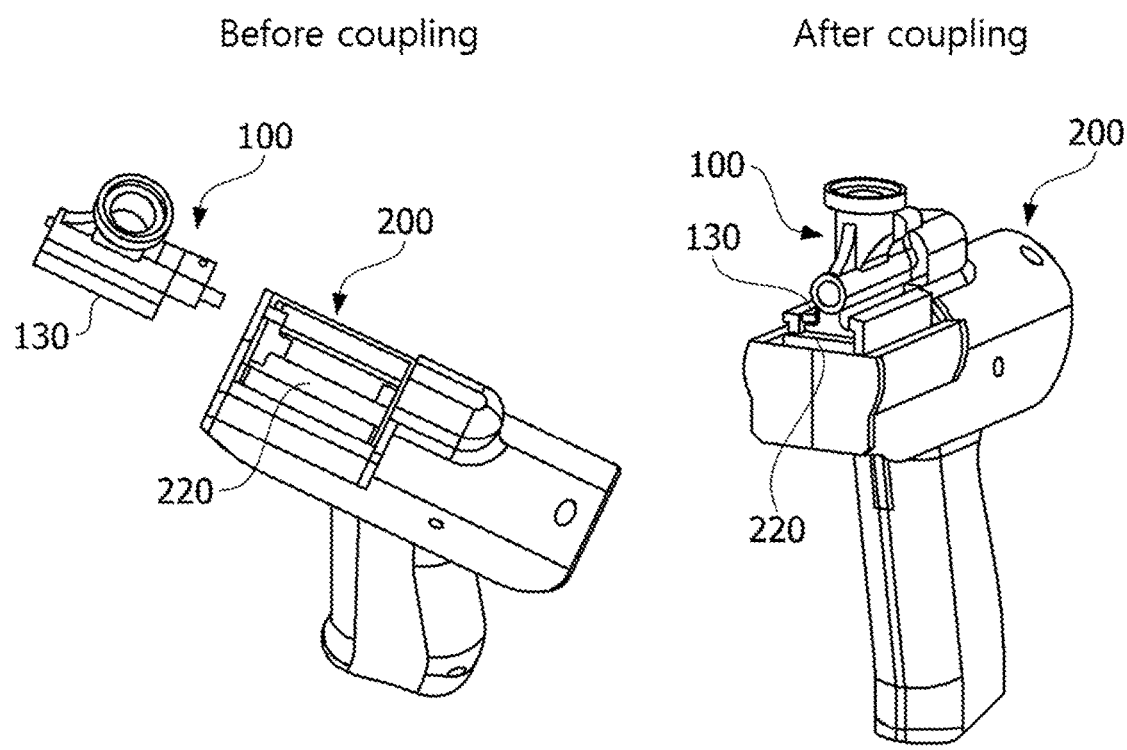
Figure 7:
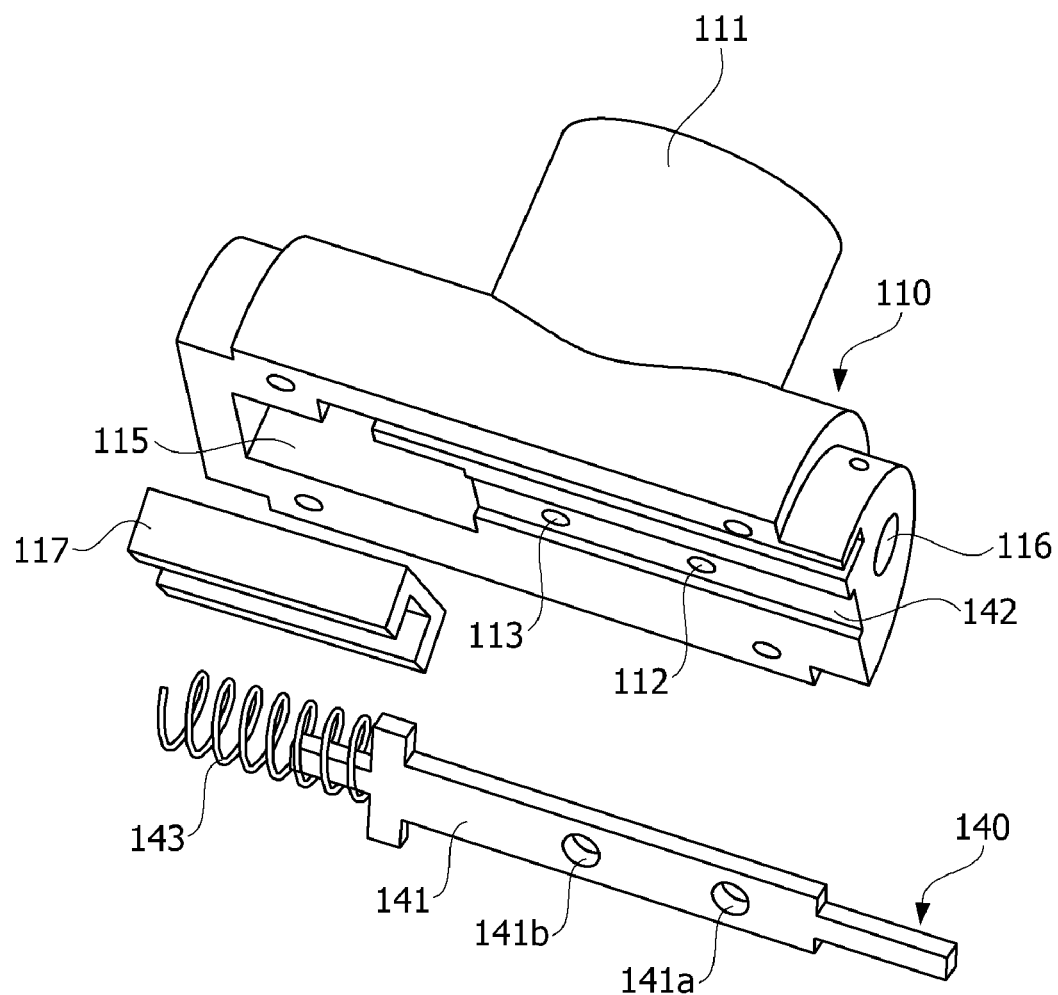

The sprayer main body coupling unit 220 is provided at one end of the sprayer main body 200 to serve to couple the dispenser coupling unit 130 to the sprayer main body 200. The sprayer main body coupling unit 220, as shown in FIG. 6, may be implemented in a groove type so that the dispenser coupling unit 130 provided in the dispenser 100 can be accommodated in the groove.

The coupling between the sprayer main body coupling unit 220 and the dispenser coupling unit 130 will be described with reference to FIG. 11. The sprayer main body coupling unit 220 includes: magnets 221 mounted in magnet fixing grooves 222, the magnets being detachably coupled with the magnets 131 mounted in the dispenser coupling unit 130 by magnetic force; and a plurality of protrusions 223 inserted into the coupling grooves 133 of the dispenser coupling unit 130 to prevent the radial-directional movement, which may be caused by the coupling through only the magnetic force. Therefore, the sprayer main body coupling unit 220 is coupled with the dispenser coupling unit 130 through the coupling through the magnetic force and the coupling between the coupling grooves 133 and the protrusions 223.

In addition, as shown in FIG. 12, the sprayer main body coupling unit 220 according to the present embodiment includes: vibrator operator through holes 224 through which vibrator operators (e.g., spring switches) inducing the operation of the vibrators provided in the dispenser 100 pass; a transfer shaft through hole 225 through which the transfer shaft 260*a* of the horizontal transfer movement unit 260 passes; and a main air connection tube 226 for connecting the connection tube 123, which connects the air movement and mixing tube 122 of the dispenser 100 and the air supply tube 250 of the main body 200, to the air supply tube 250.

Again referring to FIG. 10, the switch unit 230 may include: a main switch 230*a* for operating the air generation unit 240 to continuously move the air toward the conduit mounted in the conduit mount unit 121; and an operation switch 230*b* for operating the horizontal transfer movement unit 260 to spray the powder by the flow of air generated according to the operation of the main switch 230*a*, thereby simultaneously performing the communication between the first passage 122*b* and the air inlet 112 and the communication between the second passage 122*c* and the powder discharge port 113.

With respect to the operation of the switch unit 230, when a user presses the main switch 230*a*, the air continuously moves into the conduit mounted in the conduit mount unit 121 to prevent the inflow of the water into the conduit. The powder is highly hygroscopic due to its property, and thus the powder clumps together in the presence of even a small amount of water, and the conduit is clogged with such clumping. However, according to the present invention, the air continuously moves in a direction of the conduit during the operation of the main switch 230a, thereby fundamentally preventing the backflow of water to the conduit.

Here, when the user presses the operation switch 230b, the horizontal transfer movement unit 260 is operated to move the slider 141, thereby inducing the spray of the powder through the conduit. In this case, the dispenser 100 may vibrate through the vibrators installed in the dispenser 100 by the vibrator operation unit 280.

The air generation unit 240 may be implemented by a piston or a diaphragm type air pump 240a, which can induce the flow of air for performing the discharge, mixing, and spray of the powder in the container accommodation unit 111 of the dispenser 100 and blocking the inflow of the water into the conduit.

Furthermore, the air generation unit 240 may further include a heating apparatus 240*b* for drying the water of the air supplied to the dispenser 100. Therefore, the above-described clumping of the powder due to the water can be prevented. The heating apparatus may be implemented by, for example, a semiconductor or a heating line.

The horizontal transfer movement unit 260 may be implemented by a solenoid or a cam 260*b* having a transfer shaft 260*a*. When the operation switch 230*b* is operated, the transfer shaft 260*a* pushes the slider 141 of the opening and closing control unit 140 in the front direction (the elastomer of the opening and closing control unit is compressed), thereby inducing the spray of the powder.

Furthermore, the sprayer main body 200 may include a controller 270 (e.g., a microcomputer-based PCB controller) for controlling the flow rate of the air pump 240*a*, the operation time of the vibrators, the operation speed of the horizontal transfer movement unit 260, the temperature of the heating apparatus 240*b*, and the operation and charging state of the power unit 210.

The sprayer main body 200 may include vibrators for vibrating the powder in the container accommodation unit 111.

The sprayer main body 200 may include a vibrator operation unit 280 for the supply of power for the operation of the vibrators provided in the main body 200 or the vibrators provided in the dispenser 100. The vibrator operation unit 280 is in contact with the electrode pins E inserted into the dispenser coupling unit 130 while interlocking with the operation switch 230*b*, thereby supplying power to the vibrators to induce the operation of the vibrators.

For example, the vibrator operation unit 280 may be implemented by a spring switch for the supply of power to the vibrators.

In addition, the sprayer main body 200 may include an LED lamp 290 displaying the operation state of the apparatus.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

Explanation of reference numerals

| | |
|---|---|
| 100: dispenser | 110: dispenser upper part |
| 111: container accommodation unit | |
| 112: air inlet | |
| 113: powder discharge port | 114: vibrator frame |
| 115: fixing plate frame | 116: holding pin hole |
| 120: dispenser lower part | |
| 121: conduit mount unit | |
| 122: air movement and mixing tube | |
| 123: connection tube | |
| 124: air distributor | |
| 130: dispenser coupling unit | |
| 131: magnet | 132: magnet fixing groove |
| 133: coupling groove | |
| 134: holding pin fixing groove | |
| 135: electrode pin fixing hole | |
| 136: transfer shaft through hole | |
| 137: connection tube through hole | |
| 140: opening and closing control unit | |
| 141: slider | 142: slider guide groove |
| 143: elastomer | 200: sprayer main body |
| 210: power unit | |
| 220: sprayer main body coupling unit | |
| 230: switch unit | 240: air generation unit |
| 250: air supply tube | |
| 260: horizontal transfer movement unit | |
| 270: controller | 280: vibrator operation unit |
| 290: LED lamp | |

What is claimed is:

1. A dispenser for powder spray detachably installed on a sprayer main body, which generates a flow of air for powder spray, to spray a powder to a target site using the flow of air supplied from the sprayer main body, the dispenser for powder spray comprising:

a dispenser coupling unit that detachably couples the dispenser to the sprayer main body, the dispenser coupling unit comprising a connection tube through hole;

a conduit mount unit provided in one end of the dispenser to accommodate a conduit for guiding the powder to a target site;

a container accommodation unit provided in an upper end of the dispenser to accommodate a container containing the powder;

a powder discharge port provided in a lower end of the container accommodation unit to transfer the powder in the container accommodation unit to a lower space;

an air inlet formed to be spaced from the powder discharge port by a predetermined distance to transfer air to the container accommodation unit;

an air movement and mixing tube comprising: a guide tube for guiding the flow of air supplied from a connection tube from the sprayer main body toward the conduit mount unit; a first passage extended from the guide tube toward the air inlet to guide the air inside the guide tube toward the container accommodation unit; and a second passage extended from the guide tube toward the powder discharge port to accommodate the powder, which has passed through the powder discharge port, in the guide tube; and an opening and closing control unit provided between the air movement and mixing tube and the container accommodation unit, the opening and closing control unit configured to move back and forth to shift the locations of two holes that are provided, thereby simultaneously opening and closing the communication between the first passage and the air inlet and the communication between the second passage and the powder discharge port, and wherein the dispenser maintains constant fluid communication of air from the connection tube through hole through the connection tube and past the guide tube regardless of whether the opening and closing control unit is in an open or closed position.

2. The dispenser for powder spray of claim 1, further comprising an air distributor inserted inside the air movement and mixing tube and having two holes for guiding the flow of air supplied from the sprayer main body toward the first passage and the conduit mount unit, separately.

3. The dispenser for powder spray of claim 1, wherein the sprayer main body comprises:
   a power unit that supplies power to the sprayer main body;
   a main body coupling unit coupled with the dispenser coupling unit;
   a switch unit inducing the spray of the powder;
   an air generation unit for generating the flow of air in the apparatus according to the operation of the switch unit; and
   an air supply tube extended from the air generation unit to guide the generated flow of air to the air movement and mixing tube.

4. The dispenser for powder spray of claim 1, wherein the sprayer main body comprises:
   a power unit for supplying power to the sprayer main body;
   a main body coupling unit coupled with the dispenser coupling unit;
   a switch unit inducing the spray of the powder;
   an air generation unit for generating the flow of air in the apparatus according to the operation of the switch unit;
   an air supply tube extended from the air generation unit to guide the generated flow of air to the air movement and mixing tube; and
   a horizontal transfer movement unit that horizontally transfers the opening and closing control unit.

5. The dispenser for powder spray of claim 1, wherein vibrators for vibrating the powder in the container accommodation unit are installed adjacent to the container accommodation unit.

6. The dispenser for powder spray of claim 1, wherein vibrators for vibrating the powder in the container accommodation unit are provided in the main body.

7. A powder sprayer comprising the dispenser for powder spray detachably installed on a sprayer main body of claim 1.

* * * * *